United States Patent
Shingo

(10) Patent No.: US 7,187,962 B2
(45) Date of Patent: Mar. 6, 2007

(54) BIOLOGICAL OPTICAL MEASURING INSTRUMENT

(75) Inventor: Kawasaki Shingo, Matsudo (JP)

(73) Assignee: Hitachi Medical Corporation, Tokyo (JP)

( * ) Notice: Subject to any disclaimer, the term of this patent is extended or adjusted under 35 U.S.C. 154(b) by 492 days.

(21) Appl. No.: 10/482,579

(22) PCT Filed: Jun. 28, 2002

(86) PCT No.: PCT/JP02/06563

§ 371 (c)(1),
(2), (4) Date: Dec. 29, 2003

(87) PCT Pub. No.: WO03/002004

PCT Pub. Date: Jan. 9, 2003

(65) Prior Publication Data

US 2004/0242979 A1 Dec. 2, 2004

(30) Foreign Application Priority Data

Jun. 28, 2001 (JP) .............................. 2001-195891

(51) Int. Cl.
*A61B 5/00* (2006.01)
(52) U.S. Cl. .................................. 600/322; 600/336
(58) Field of Classification Search ................ 600/323, 600/336, 328
See application file for complete search history.

(56) References Cited

U.S. PATENT DOCUMENTS 5,555,882 A * 9/1996 Richardson et al. ........ 600/336
6,083,157 A * 7/2000 Noller ........................ 600/310
6,393,311 B1 * 5/2002 Edgar et al. ................. 600/323

FOREIGN PATENT DOCUMENTS

CN 1225562 8/1999
WO WO98/02087 1/1998

OTHER PUBLICATIONS

Algorithm for Real—Time Detection of QRS Complex in ECG Signal, Wang et al, Space Medicine & Medical Engineering, vol. 8, No. 1, Mar. 1995.

* cited by examiner

Primary Examiner—Eric F. Winakur
Assistant Examiner—Jack Lin
(74) Attorney, Agent, or Firm—Antonelli, Terry, Stout and Kraus, LLP.

(57) ABSTRACT

In a biological optical measuring instrument, when displaying a biological variation in a predetermined region of a subject through irradiating light to the subject and processing light signals obtained by detecting the transmitting light, the light signals of a plurality of sections having a predetermined time interval are extracted, section data are prepared from the respective extracted light signals, the plurality of the prepared section data are added and averaged, prior to preparing averaged section data for the predetermined time interval a light signal section containing noise components is specified from differential values of the extracted light signals and the section data of the light signal containing the noise components is excluded from the averaging operation, thereby, a biological optical measuring instrument is provided which permits to remove the section data containing noise components are automatically removed through computation without relying upon visual observation, to obtain highly reliable measurement result quickly and to display the same.

20 Claims, 5 Drawing Sheets

BIOLOGICAL OPTICAL MEASURING INSTRUMENT

FIELD OF THE INVENTION

The present invention relates to a biological optical measuring instrument and, in particular, relates to a signal processing therefor.

BACKGROUND OF THE INVENTION

The biological optical measuring instrument is an instrument for obtaining information such as blood circulation, blood circulation dynamics and hemoglobin variation inside a living body by irradiating light having predetermined wavelengths into the living body and by measuring amount variation in light transmitted through the living body, in particular, a biological optical measuring instrument which is designed for obtaining blood stream information in a comparatively broad area in a form of a topography has been expected, for example, for a research of brain functions such as local center identification at the time of epilepsy stroke and clinical applications.

As an example of the clinical applications, a measurement result of hemoglobin variation in a brain at the time of performing motion and language task by utilizing a method called brain blood stream mapping method using near-infrared light is reported in WATANABE Eiju, "Brain Blood Stream Mapping Method Using Near-Infrared light" (CLINICAL NUEROSCIENCE Vol. 17, No. 11, 1999-11, P1280–1281, Cyugaiigakusya). In this method, in order to capture the hemoglobin variation in the brain, after performing a plurality of tests on respective tasks, averages of the respective values are calculated. This calculation of adding and averaging is performed for enhancing S/N ratio, because the hemoglobin variation in the brain, which is obtained through physiological stimulations such as the motion and language task, is at most about 5%.

In contrast to the fact that the amount of variation in optical signals due to hemoglobin, which is measured with these biological optical measurements, is in an order of a few percent, the amount of variation in optical signals caused by body movement reaches more than 50%, which is superposed in a spike like noise on an optical signal to be measured. Such a spike like noise can be separated by visual observation in a case of a single measurement data, which does not require the adding and averaging calculation, because such appears in a steep peak, however, in a case where the variation in the amount of hemoglobin is determined by the above referred to adding and averaging calculation, since the peak value due to the noise is averaged and is superposed on the measured data, it was difficult to separate the noise from the actual measured data, which has prevented accurate diagnosis.

In conventional biological optical measurements, in order to process measured data in which noises are contained, there were no methods other than a method in which the noises are recognized from the measured data through visual observation and a portion corresponding to the noises is removed from the result of the averaged hemoglobin amount variation, and of which method has been extremely impeded real-time data display property.

Accordingly, an object of the present invention is to provide a biological optical measuring instrument and a method thereof which permits to detect measured data containing noise components by utilizing a characteristic of the noise components which appear in steep peaks and to automatically remove through computation the optical signal portion containing the noise components from the measured result to be determined without relying upon the visual observation.

Further, another object of the present invention is to provide a biological optical measuring instrument and a method thereof which permits to quickly acquire highly reliable measurement result and thereby to provide valuable information for research and diagnosis.

DISCLOSURE OF THE INVENTION

The biological optical measuring instrument of the present invention which achieves the above objects comprises a light generating unit which irradiates light having a predetermined wavelength to a subject, a light detecting unit which detects light which is irradiated from the light generating unit and is transmitted through the subject and a signal processing unit which analyzes optical signals detected by the light detecting unit and prepares biological information including blood stream in the subject, wherein the signal processing unit includes means for detecting noise components contained in the detected optical signals and means for removing an optical signal portion containing the detected noise components from the optical signals.

Therefore, according to the biological optical measuring instrument of the present invention, through the provision of the means for detecting existence and absence of noise components in the detected optical signals as well as the means for removing the optical signal portion containing the noise components from the detected optical signals, the removing work of the optical signal portion containing the noise components which was performed conventionally through visual observation, is automated which permits to display quickly an accurate measurement result.

Still further, in the biological optical measuring instrument of the present invention, the detection of the noise components in the optical signals can be performed in such a manner that differential values of the optical signals obtained in time-course are determined and the existence of noises is judged when the differential values exceed a predetermined threshold value. Through the judgment of using the differential values, the spike shaped noise being contained due to body movement of the subject can be effectively detected and the influence due to the spike shaped noise can be eliminated.

Moreover, the biological optical measuring instrument of the present invention, the signal processing unit includes means for extracting optical signals in a plurality of sections having a predetermined time interval from optical signals obtained along the time axis and for preparing section data from the respective extracted optical signals, means for detecting and removing section data containing noise components among the extracted and prepared section data and means for performing adding and averaging process using the not removed section data among the plurality of the section data and for preparing averaged section data having a predetermined time interval.

With regard to the measured data obtained by the addition and averaging processing, in which the noise components tend to be buried, the noise components are detected in advance in the present invention and the section data containing the noise components are removed from the object for the addition and averaging processing, thereby, reliability of the addition and averaging processing is enhanced and accurate measurement data can be obtained.

BEST MODES FOR EMBODYING THE INVENTION

Hereinbelow, the biological optical measuring instrument of the present invention will be explained based on an embodiment in which the present invention is applied to an instrument for displaying a variation of hemoglobin amount in a predetermined region in an image. The present instrument is provide with a function in which, when tasks such as motion and language causing brain activity are given for a subject, measures a variation of hemoglobin amount in the brain (concentration variation of oxygenated hemoglobin, concentration variation of deoxygenated hemoglobin and concentration variation of total hemoglobin) and displays the variations at every measurement position.

Figure 1:
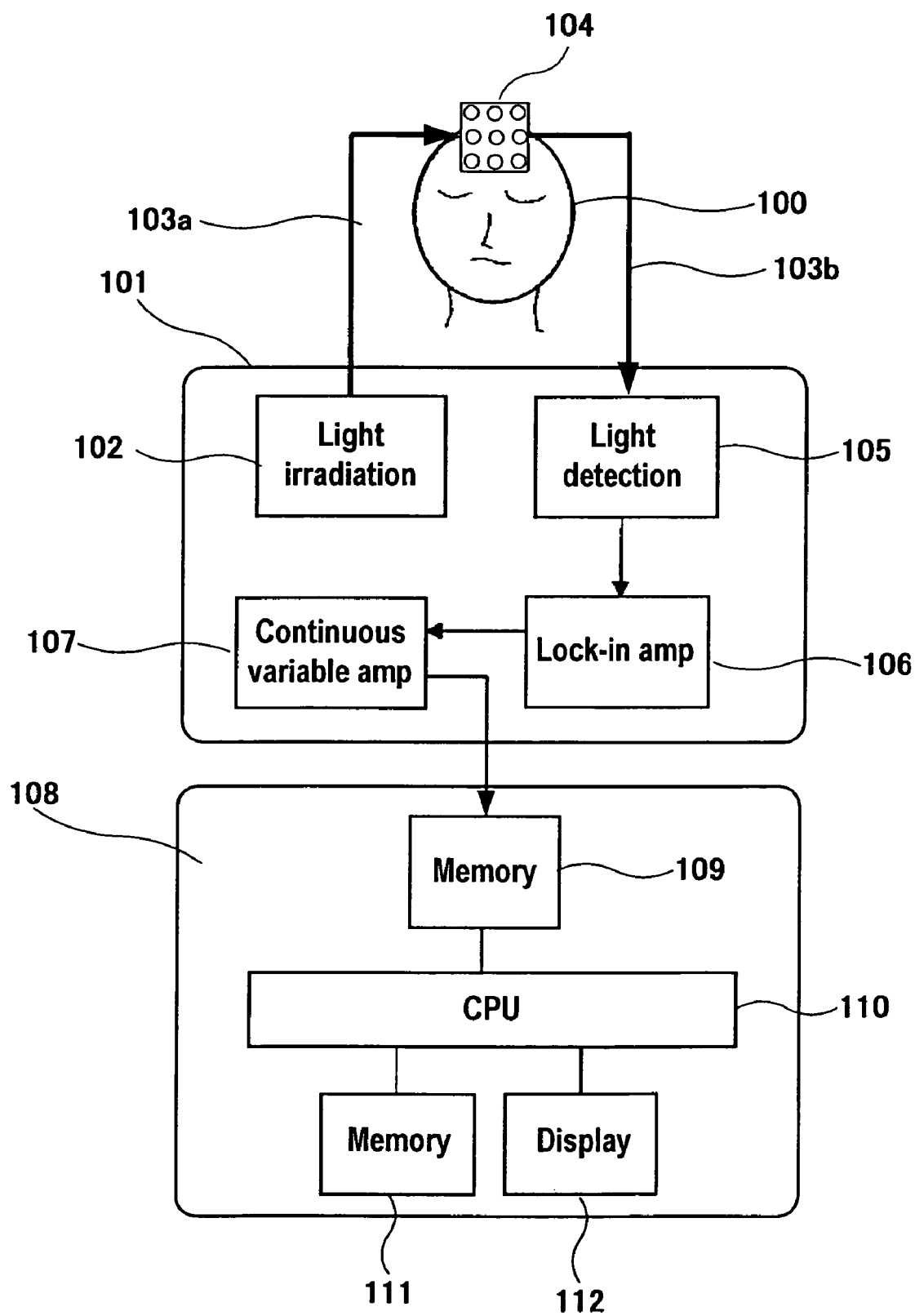
FIG. 1 is a block diagram showing an entire constitution of an instrument for displaying variation of hemoglobin amount in an image and representing an example of biological optical measuring instruments to which the present invention is applied.

FIG. 1 is a diagram showing an entire constitution of an instrument to which the present invention is applied, as shown in the drawing, the present instrument is provide with a light irradiating and detecting unit 101 which irradiates light at a predetermined region of a subject 100 as well as detects light transmitted through the predetermined region at every plurality of detection positions and takes out biological information including position information in optical signals, and a signal process unit 108 which processes the detected optical signals and displays variation information of hemoglobin, oxygen saturation degree and cytochrome concentration in such as numerical values and topography.

The light irradiation and detecting unit 101 is provide with a light irradiation unit 102 which generates light having a predetermined wavelength, specifically, near infrared light, a light detecting unit 105 which detects light transmitted through the subject 100 and converts the detected light into electrical signals, a probe 104 which holds the top ends of optical fibers 103a and 103b connected respectively to the light irradiation unit 102 and light detecting unit 105 in a predetermined arrangement and causes to contact the optical fibers to the subject 100, a lock-in amplifier 106 which lock-in detects the electrical signals from the light detecting unit 105, a continuous variable amplifier 107 which amplifies the output from the lock-in amplifier 106 and an A/D converter not shown. As the light detecting unit 105, it is preferable to use a photo diode, in particular, an avalanche photo diode, which can realize light measurement of high sensitivity.

In the drawings, a single piece of the irradiation optical fiber 103a and detection optical fiber 103b is illustrated, however, each of the optical fibers is constituted by a plurality of optical fibers, for example, they are constituted in 3×3 mode or 4×4 mode and their top ends are arranged alternatively at the grid points of the probe 104 so that each pair of irradiation and detection optical fibers constitutes one channel. Depending on the number of the irradiation optical fibers, the light irradiation unit 102 generates light modulated by a plurality of frequencies. Further, the lock-in amplifier 106 selectively detects the modulated signals corresponding to irradiation positions and wavelengths using the plurality of modulation frequencies as reference frequencies. Thereby, optical signals at respective measurement positions (positions between top ends of the irradiation optical fibers and of the detection optical fibers) can be detected.

The continuous variable amplifier 107 is provided for leveling the signals from the respective channels. Further, although not illustrated, the signals being leveled are time integrated for every channel and held in a sample hold circuit, thereafter, sent out to the A/D converter.

The signal process unit 108 is provided with a memory 109 which temporarily stores digital signals sent from the light irradiation and detection unit 101, a CPU 110 which performs a variety of computation and analysis such as variation of hemoglobin concentration by using the digital signals, another memory 111 which stores the computation result in the CPU 110, a display unit 112 which displays the computation result, for example, the variation of the hemoglobin amount in such as line diagram like a contour and colored image, and an input unit not shown which permits to input in the CPU a variety of information such as conditions necessary for the measurement and information of the subject.

The signal process unit 108 can be constituted integral with the light irradiation and detection unit 101 in the instrument, however, alternatively can be realized by a general use personal computer.

Other than the functions of computing light amount variation depending on the variation of hemoglobin amount before and after giving tasks to the subject and of performing the addition and averaging calculation of the measured values obtained in a plurality of measurements, the CPU 110 detects noises contained in a variation curve of the light amount and removes a portion of measured value containing noise components from the variation curve, of which function will be explained later.

Now, the operation of the instrument with the above constitution and the processing performed by the signal process unit 108 will be explained.

Under a condition where the probe 104 is attached on the head (for example, the front head) of the subject 100, while giving intermittently tasks to the subject 100, light is irradiated from the light irradiation unit 102 and the light detection unit 105 detects the transmitted irradiation light through the subject 100. A part of the transmitting light is absorbed by specific pigments in the living body, for example, hemoglobin, and shows a light amount reflecting the hemoglobin concentration. Further, since depending on the conditions whether tasks are given or not, the blood stream in the brain changes, the hemoglobin amount varies correspondingly.

The variation of the light amount depending upon the change in hemoglobin amount is detected for every detection position by the light detection unit 105 and converted into electrical signals which are lock-in detected by the lock-in amplifier 106 and inputted in the signal process unit 108 as the signals at the respective measurement positions. The signals inputted in the signal process unit 108 are stored in the memory 109, thereafter, are converted into signals (hemoglobin signals) corresponding to hemoglobin concentration in the CPU 110.

Figure 2:
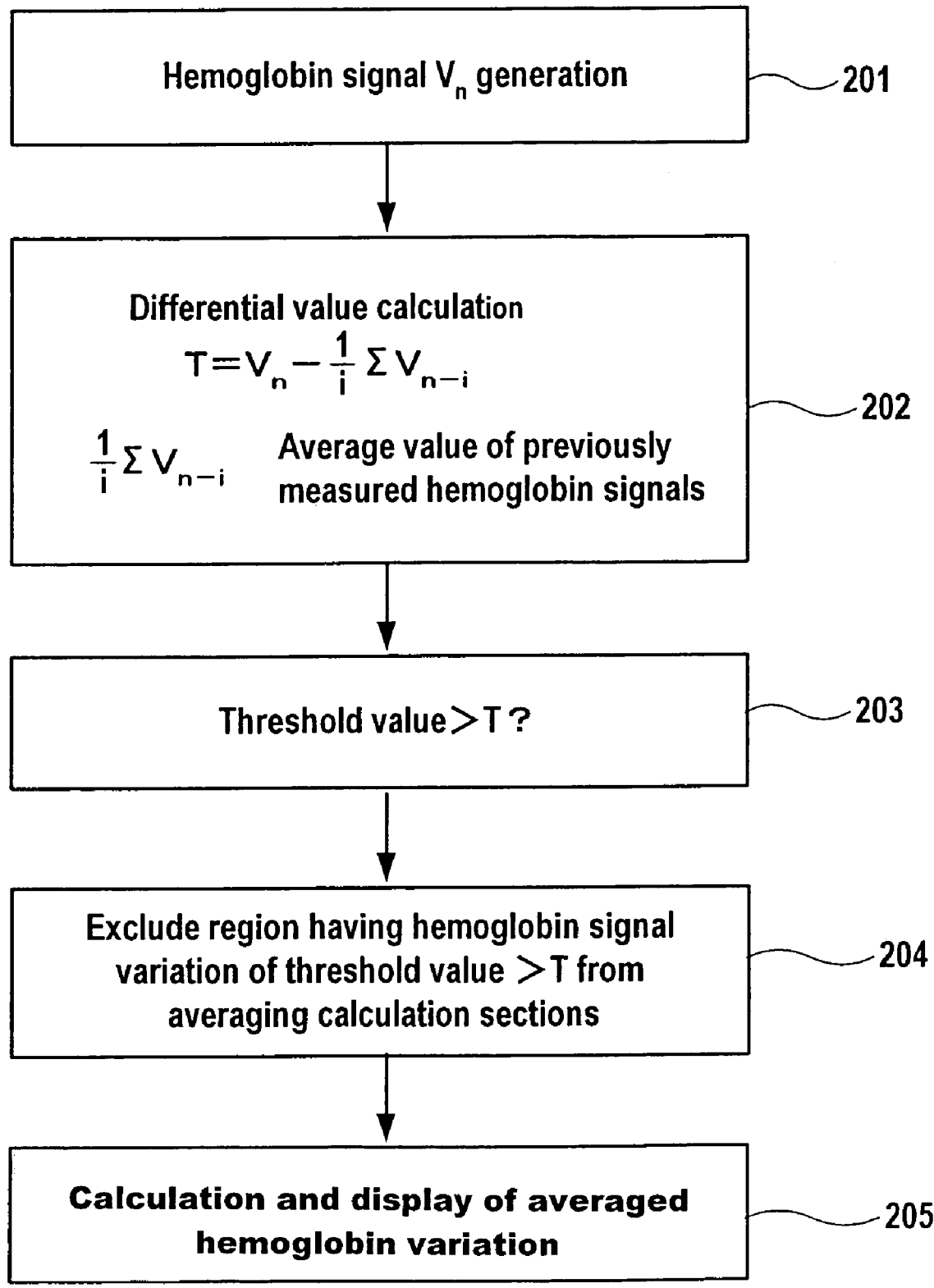
FIG. 2 is a processing flow of the present invention, which is executed in a signal process unit as shown in FIG. 1.

Now, the processing performed by the CPU 110 will be explained with reference to FIG. 2.

At first, the CPU 110 determines hemoglobin concentration for every channel based on the detected light amount through computation according to the following equations (1)~(3) (refer to, Atsushi MAKI et al "Visualizing human motor activity by using non-invasive optical topography" (Frontiers Med.Biol.Engng.Vol.7, No.4 pp 285–297(1996)), and the hemoglobin signals are generated (step 201). Namely, detected light amount R(λ) of wavelength λ at respective measurement positions is represented approximately by the equation (1). Likely, detected light amount $R^s(\lambda)$ at the time of task execution is represented by the equation (2);

$$-\ln\frac{R(\lambda)}{R_0(\lambda)} = \varepsilon_{oxy}(\lambda)C_{oxy}d + \varepsilon_{deoxy}(\lambda)C_{deoxy}d + \alpha(\lambda) + s(\lambda) \quad (1)$$

$$-\ln\frac{R^s(\lambda)}{R_0(\lambda)} = \varepsilon_{oxy}(\lambda)C^s_{oxy}d + \varepsilon_{deoxy}(\lambda)C^s_{deoxy}d + \alpha(\lambda) + s(\lambda) \quad (2)$$

In the equations, $R_0(\lambda)$ is irradiation light amount, $\varepsilon_{oxy}(\lambda)$, $\varepsilon_{deoxy}(\lambda)$ are molecular extinction coefficients of oxygenated and deoxygenated hemoglobin at wavelength λ, $C_{oxy}$, $C_{deoxy}$ are concentrations of oxygenated and deoxygenated hemoglobin, d is an effective light propagation length in an active region of the cerebral cortex, $\alpha(\lambda)$ is an attenuation due to light absorption by pigments other than hemoglobin, and $s(\lambda)$ shows an attenuation due to light scattering by tissue. The superior letter "s" indicates values during the task execution.

Herein, it is considered that $\alpha(\lambda)$, $s(\lambda)$ do not change both during the task execution and non-task execution, through subtracting equation (1) from equation (2), a variation of hemoglobin amount can be obtained according to the following equation (3);

$$-\ln\frac{R^s(\lambda)}{R(\lambda)} = \varepsilon_{oxy}(\lambda)\Delta C_{oxy} + \varepsilon_{deoxy}(\lambda)\Delta C_{deoxy} \quad (3)$$

Wherein, $\Delta C_{oxy} = (C^s_{oxy} - C_{oxy})d$ $\Delta C_{deoxy} = (C^s_{deoxy} - C_{deoxy})d$ $\Delta C_{total} = \Delta C_{oxy} + C_{deoxy}$ Further, when determining $\Delta C_{oxy}$, $\Delta C_{deoxy}$, $\Delta C_{total}$ independently, the left-hand member of equation (3) has to determined with regard to at least two wavelengths and by solving the simultaneous equations with regard to the two wave lengths the respective concentration variations can be determined.

Subsequently, using the hemoglobin signals (for example, hemoglobin signal corresponding to the total hemoglobin amount) which were determined as explained above, the CPU 110 performs the adding and averaging of the data corresponding to a plurality of task execution sections and determines hemoglobin variation during the task execution (step 205).

Figure 3:
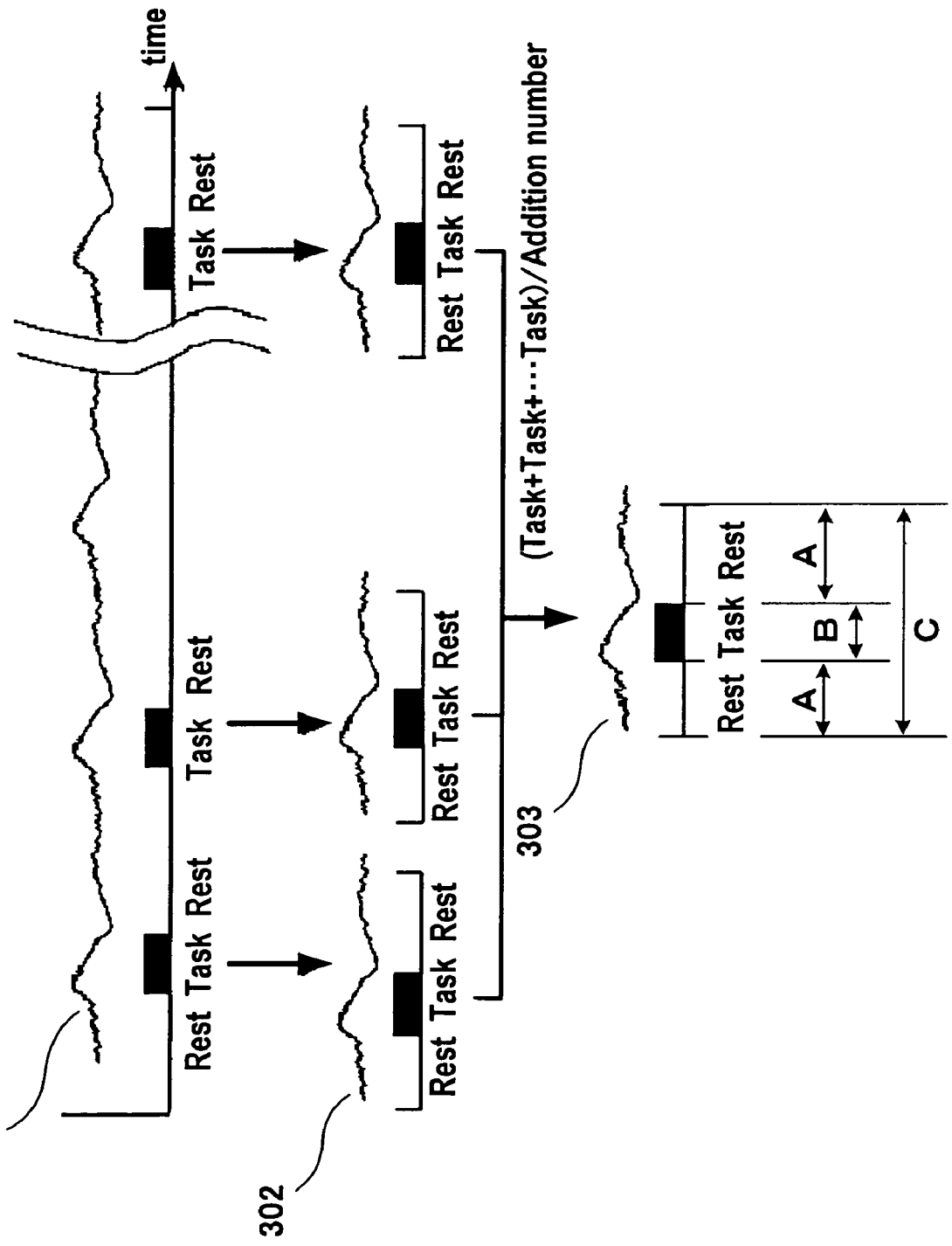
FIG. 3 is a diagram for explaining addition and averaging processing executed in the signal process unit as shown in FIG. 1.

A manner of obtaining the average is illustrated in FIG. 3. As shown in the drawing, the CPU 110 cuts out data having a predetermined interval C, for example 40 sec, containing the task execution section B, for example 10 sec, from the hemoglobin signals 301 representing time course data and obtains data 302 corresponding to number of task times, for example 5 times (hereinbelow called as extracted section data). The cutting out process of the extracted section data 302 can be performed based on clocks in the measurement system, which manages the task execution. Namely, in order to cause the subject to perform the tasks in a predetermined interval, clocks are used, therefore, following the clocks, when the timing of the time course data acquisition and the timing of ending thereof are set, data having a predetermined length including a predetermined interval A, for example 15 sec, before and after the task execution section can be cut out.

The CPU 110 adds the plurality of extracted section data 302 extracted in the above manner and divides the sum by the number of task times, thereby an averaged section data 303 is obtained. However, if a noise of spike shape caused by a body movement is contained in any of the extracted section data, the averaged section data significantly varies due to the influence of the noise, which prevents acquisition of effective data for diagnosis. Therefore, prior to the addition and averaging process, the CPU 110 detects noise components contained in the hemoglobin signals and removes the extracted section data containing noise components so as not to be used in the addition and averaging process (steps 202~204).

Figure 4A:
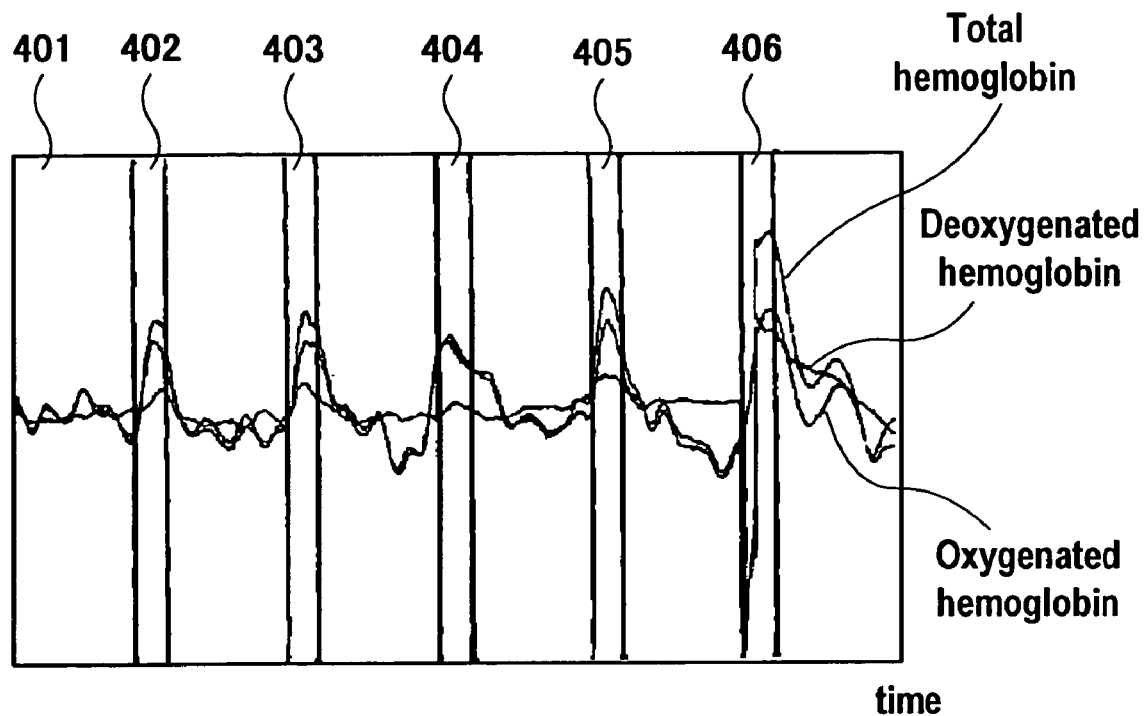
FIG. 4A is a diagram showing a variation in hemoglobin signals along time axis at the time when tasks are executed and no tasks (rest) are executed, which were measured with the instrument as shown in FIG. 1.
Figure 4B:
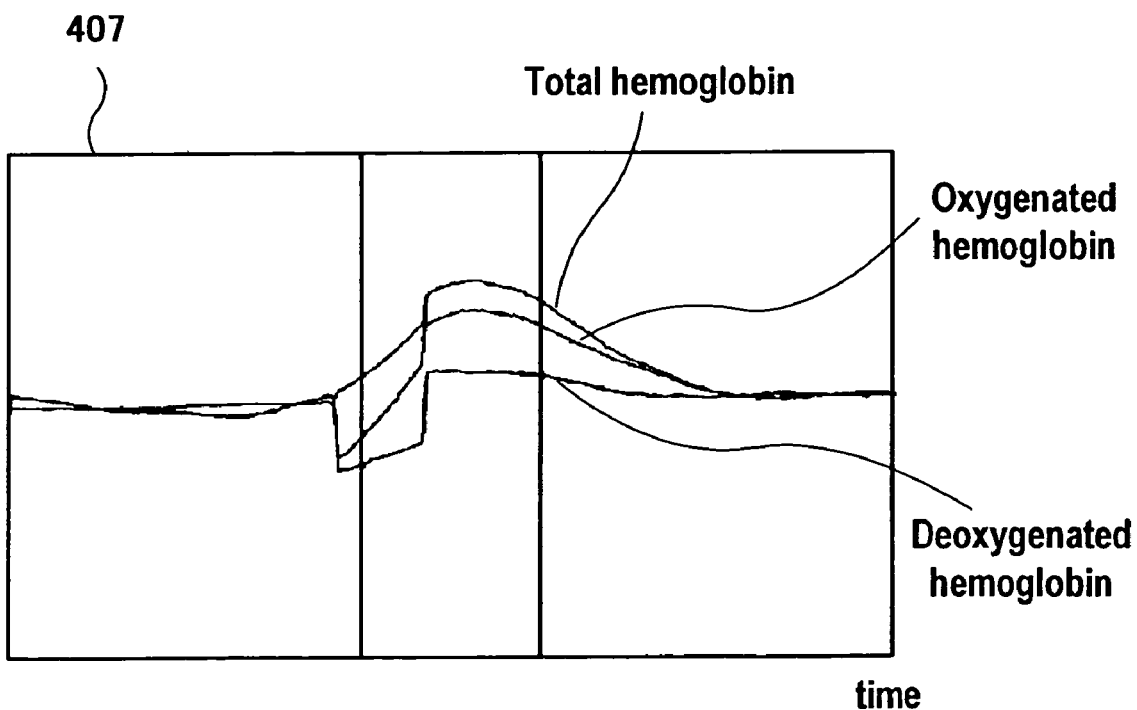
FIG. 4B is a diagram for explaining an influence of noises in the addition and averaging processing and shows a result of the addition and averaging of the hemoglobin signals as they are for entire sections each including the task executing section and having a predetermined time interval.

The above will be explained with reference to FIGS. 4A and 4B. FIG. 4A shows a graph formed by plotting the hemoglobin signals 401 along time axis. As shown in the drawing, the hemoglobin signals 401 show large values in the task executing sections 402–406 as shown in the drawing. However, in the task executing section 406, since a spike shaped noise caused by body movement is superposed, the hemoglobin signals averaged by including data of such task executing section 406 contains the steeply varying noise components as shown by 407 in FIG. 4B, therefore, a curve representing correct hemoglobin variation can not be obtained.

In order not to use such data of task executing sections containing noises for the averaging, the CPU 110 determines differential values for the respective hemoglobin signals and specifies the task executing sections containing hemoglobin signals of which differential values exceed a predetermined value (steps 202,203).

In the step 202 in which the differential values are determined by using the hemoglobin signals, a difference T between the average value of a plurality of hemoglobin signals Vn-1 which were measured prior to the objective hemoglobin signal Vn and the hemoglobin signal Vn. Namely, a calculation according to the following equation (4) is performed;

$$T = V_n - \frac{1}{i}\sum V_{n-i} \quad (4)$$

Figure 5:
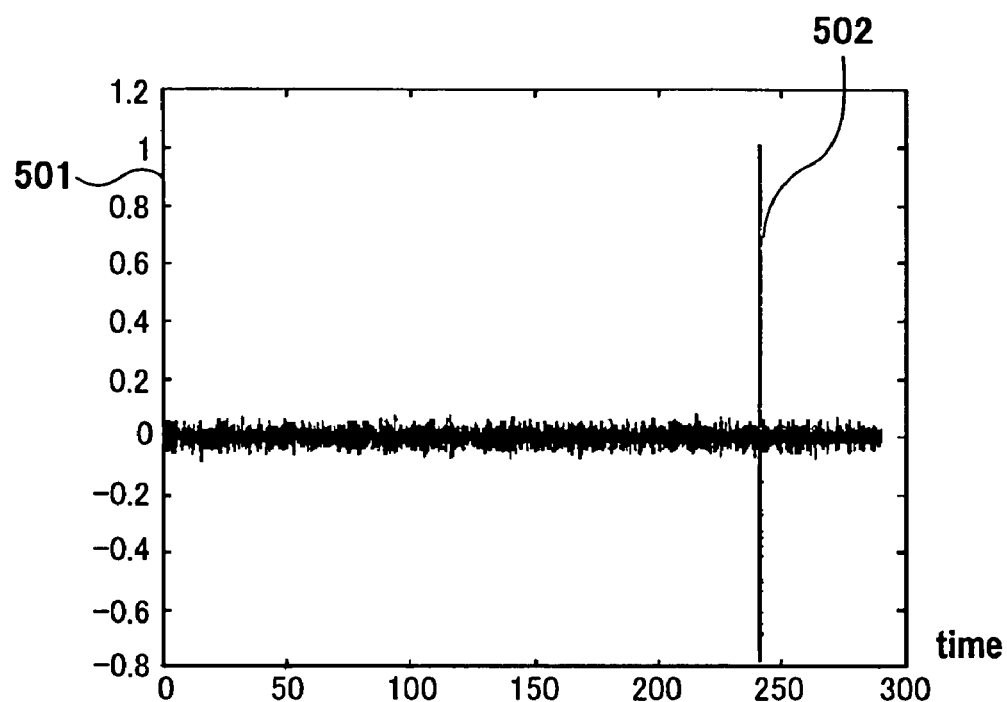
FIG. 5 is a diagram for explaining a differential processing in the present invention and shows a variation rate of the hemoglobin signals over the entire measurement period.

As shown in FIG. 5, the variation of hemoglobin amount 501 both during task execution and non-task execution is within a few percent, however, the spike shaped noise 502 caused by body movement exceeds far beyond the range of the normal variation of hemoglobin amount.

For this reason, it is judged whether or not the difference T between the objective hemoglobin signal value and the average value of the previous hemoglobin signals exceeds the threshold value (step 203). As the threshold value, a proper value, which exceeds a normal variation of hemoglobin amount, can be selected, for example, at 0.5. The threshold value can be set in advance as a constant value for the processing program in the CPU 110 or can be set optionally and occasionally by the user. As the result of the above judgment, when the difference T (absolute value) is larger than the threshold value, it is judged that noises are superposed in the hemoglobin signal, the extracted section data containing the hemoglobin signal is deleted (step 204). Thereby, the extracted section data containing noise components is removed from objects of the adding and averaging process thereafter (step 205).

Figure 6:
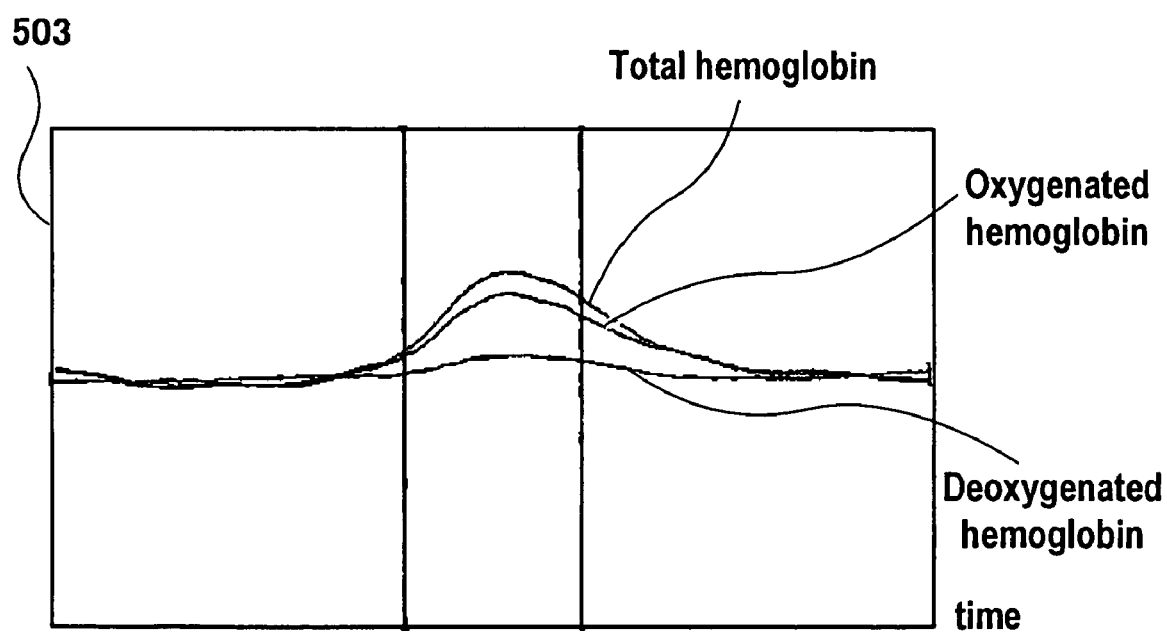
FIG. 6 is a diagram showing a result according to the present invention in which the section data containing noise components are removed and the remaining hemoglobin signals are added and averaged.

Subsequently, as has been explained above, a plurality of extracted section data not deleted are averaged, and data representing hemoglobin variation at the time of task execution is obtained. The result of averaging obtained after the steps 202~205 is shown in FIG. 6 as by 503. As will be apparent from the comparison with 407 in FIG. 4B, the hemoglobin variation curve 503 correctly reflecting the hemoglobin increase due to the task execution can be obtained.

Such a hemoglobin variation curve is obtained for every measurement position. The display unit 112 displays these curves for every measurement position in a form of graph as well as displays two dimensional image of the hemoglobin variation in a topography. Thereby, diagnostically important information such as specifying varied portions in the brain due to stimulation such as tasks and difference in the variation depending on the kind of the tasks can be obtained correctly. In the present embodiment, since the conventional noise removal by mean of the visual observation is eliminated, the measured data can be displayed in real time.

Hereinabove, as an example of the biological optical measuring instruments of the present invention, an embodiment of the instrument, which permits to display hemoglobin amount variation in an image form has been explained. The present invention is not limited to the present embodiment and can be modified in a variety of manners. For example, although in the above embodiment the measured signals are extracted as data for every section having a predetermined time interval and the data are averaged, the present invention can be applied when removing a portion containing noise components for a single measurement signal.

Further, although in the present embodiment the hemoglobin variation more than the threshold value is detected and the extracted section data containing such hemoglobin signal is removed from the addition and averaging process, the method of removing noises from the addition and averaging process is not limited to the above method.

For example, when it is judged in step 202 that the differential value (difference from the average value) T of the hemoglobin signal is larger than the threshold value, the hemoglobin signal value is removed as well as the removed hemoglobin signal value is interpolated by the hemoglobin signal values at the nearest both sides of which difference T is less than the threshold value and the interpolated extracted section data can be used for the addition and averaging process. When the number of the extracted section data is small, the above method is advantageous for preventing deterioration of S/N ratio.

Further, the hemoglobin signal value can be any amount of oxygenated hemoglobin, deoxygenated hemoglobin and total hemoglobin. Still further, the present invention can be likely applied to the variation measurement of materials other than hemoglobin, which permit measurement by the biological optical measurement, such as cytochrome a, a3 and myoglobin.

According to the present invention, since the noise components superposed on the signals to be measured are automatically detected through computation without relying upon visual observation and the section data containing the noise components are removed from the measured data, an accurate measurement data can be obtained. In particular, in order to detect noise components in the signals to be measured, because of the use of the differential value of the signal value, the spike shaped noise, which significantly affect to the adding and averaging process of the signal values can be removed effectively.

The invention claimed is:

1. A biological optical measuring instrument comprising a light generating unit which irradiates light having a predetermined wavelength to a subject, a light detecting unit which detects light which is irradiated from the light generating unit and is transmitted through the subject, and a signal processing unit which analyzes signals detected by the light detecting unit and prepares biological information including blood stream information in the subject, wherein the signal processing unit includes means for detecting spike shaped noise components contained in the detected signals in a form of steep peaks which are due to body movement by the subject, and means for removing a signal portion containing the detected spike shaped noise components from the signals.

2. A biological optical measuring instrument according to claim 1, wherein the means for detecting the spiked shaped noise components judges that the spiked shape noise components are contained in a corresponding portion of the signals, when any of differential values of the signals obtained in a time course, are more than a predetermined threshold value.

3. A biological optical measuring instrument according to claim 1 or 2, wherein the signal processing unit includes means for extracting signals in a plurality of sections having a predetermined time interval from signals obtained along the time axis and for preparing section data from the respective extracted signals, means for detecting and removing section data containing noise components among the extracted and prepared section data, and means for performing adding and averaging process using the not removed section data among the plurality of the section data and for preparing averaged section data having a predetermined time interval.

4. A biological optical measuring instrument according to claim 3, wherein the section having a predetermined time interval includes a time interval, in which a task is executed by the subject.

5. A biological optical measuring instrument according to claim 4, wherein the task executed by the subject is motion and language.

6. A biological optical measuring instrument according to claim 3, wherein the light having a predetermined wavelength is near-infrared light.

7. A biological optical measuring instrument according to claim 1 or 2, wherein the light having a predetermined wavelength is near-infrared light.

8. A biological optical measuring method comprising:
a first step of irradiating light having a predetermined wavelength to a subject from a first position of the subject and measuring the transmitting light at a second position of the subject as transmitting light signal data containing biological information in a plurality of times for a predetermined interval;
a second step of adding the plurality of measured transmitting light signal data for the predetermined time interval and determining an average value of the transmitting light signal data;
a third step of determining differences of the respective transmitting light signal data for the predetermined time interval and the average value of the light transmitting signal data for the predetermined time interval prior to the respective concerned transmitting light signal;
a fourth step of excluding transmitting light signal data for the predetermined time interval, of which a determined difference exceeds a predetermined threshold value, which is indicative of spike shaped noise components contained in the measured light transmitting signal data in the form of steep peaks which are due to body movement by the subject, for later averaging computation of the transmitting light signal data; and
a fifth step of displaying the biological information, which includes blood stream information in the subject, in a form of an image based on processing of the transmitting light signal data in the first through fourth steps.

9. A biological optical measuring method according to claim 8, wherein the light having a predetermined wavelength is near-infrared light.

10. A biological optical measuring method according to claim 8, wherein the section having a predetermined time interval includes a time interval in which a task is executed by the subject.

11. A biological optical measuring method according to claim 8, wherein the transmitting light signal data including biological information is hemoglobin concentration signal data relating to oxygenated hemoglobin, deoxygenated hemoglobin or total hemoglobin.

12. A biological optical measuring instrument comprising a light generating unit which irradiates light having a predetermined wavelength to a subject, a light detecting unit which detects light which is irradiated from the light generating unit and is transmitted through the subject, a signal processing unit which analyzes signals detected by the light detecting unit and prepares biological information including blood stream information in the subject, a first memory means which store a first part of the biological information obtained when the subject is executing a task, a second memory means which store a second part of the biological information obtained when the subject is not executing the task, evaluation means which evaluates a hemoglobin variation when the subject is executing the task based on difference information of the biological information stored respectively in the first and second memory means, and control means which controls the light generating unit, the light detecting unit, the signal processing unit, the first memory means, the second memory means and the evaluation means, wherein the signal processing means includes means for detecting spike shaped noise components contained in the detected signals in a form of steep peaks which are due to body movement of the subject, and means for removing a signal portion containing the detected spike shaped components from the signals.

13. A biological optical measuring instrument according to claim 12, wherein the noise components detecting means determines differential values of the signals obtained time-sequentially and judges, when the differential values exceed a predetermined value, that the spike shaped noise components are contained in the concerned portion of the signals.

14. A biological optical measuring instrument according to claim 13, wherein the noise components detecting means includes means for determining an average value of a plurality of signals prior to signals in which whether the spiked shaped noise components are contained is to be judged, means for further determining a difference value between the determined average value and the signals in which whether the spiked shaped noise components are contained is to be judged, and means for judging, when the difference value is larger than a predetermined value, that the spiked shaped noise components are contained in the signals.

15. A biological optical measuring instrument according to claim 12, wherein the first part of the biological information is prepared time-sequentially during task executing period when the subject is executing a task and the second part of the biological information is prepared time-sequentially during non-task executing period when the subject is not executing a task.

16. A biological optical measuring instrument according to claim 15, wherein the control means, while causing to repeat light detection during the task executing period and during the non-task executing period, prepares biological information in combination of a plurality of task executing periods and non-task executing periods.

17. A biological optical measuring instrument according to claim 12, wherein each interval of the plurality of task executing periods and non-task executing periods is the same and the respective biological information in the plurality of task executing periods and non-task executing periods are averaged for evaluating the hemoglobin variation.

18. A biological optical measuring instrument according to claim 17, wherein when the noise components detecting means judges that the spiked shaped noise components are contained in the concerned signals, the concerned signals are removed for the averaging process.

19. A biological optical measuring instrument according to claim 17, wherein when the noise components detecting means judges that the spiked shaped noise components are contained in the concerned signals, the concerned signals are removed for the averaging process and the removed signals portion is interpolated by hemoglobin values at immediate both sides of the removed signals portion for the averaging process.

20. A biological optical measuring instrument according to claim 12, wherein the task executed by the subject is motion and language.

* * * * *